United States Patent
Simmons et al.

(10) Patent No.: US 9,913,908 B2
(45) Date of Patent: *Mar. 13, 2018

(54) TRANSDERMAL PHARMACEUTICAL BASES FOR TREATING EAR DISORDERS

(71) Applicant: Professional Compounding Centers of America (PCCA), Houston, TX (US)

(72) Inventors: Chris V. Simmons, Sugar Land, TX (US); Daniel Banov, Sugar Land, TX (US)

(73) Assignee: Professional Compounding Centers of America, Houston, TX (US)

( * ) Notice: Subject to any disclaimer, the term of this patent is extended or adjusted under 35 U.S.C. 154(b) by 175 days.

This patent is subject to a terminal disclaimer.

(21) Appl. No.: 14/830,927

(22) Filed: Aug. 20, 2015

(65) Prior Publication Data
US 2016/0051681 A1 Feb. 25, 2016

Related U.S. Application Data

(60) Provisional application No. 62/039,780, filed on Aug. 20, 2014, provisional application No. 62/039,794, filed on Aug. 20, 2014.

(51) Int. Cl.
*A61K 47/34* (2017.01)
*A61K 47/44* (2017.01)
*A61K 47/24* (2006.01)
*A61K 9/00* (2006.01)
*A61K 47/12* (2006.01)
*A61K 36/889* (2006.01)
*A61K 36/47* (2006.01)

(52) U.S. Cl.
CPC ............ *A61K 47/34* (2013.01); *A61K 9/0014* (2013.01); *A61K 9/0046* (2013.01); *A61K 36/47* (2013.01); *A61K 36/889* (2013.01); *A61K 47/12* (2013.01); *A61K 47/24* (2013.01); *A61K 47/44* (2013.01)

(58) Field of Classification Search
CPC ..................................................... A61K 36/00
See application file for complete search history.

*Primary Examiner* — Qiuwen Mi
(74) *Attorney, Agent, or Firm* — David G. Woodral; Scott R. Zingerman; Gable Gotwals

(57) ABSTRACT

The present disclosure refers to transdermal pharmaceutical bases that include a synergistic combination of a silicone base with a natural permeation enhancement composition (NPE). Further, these transdermal pharmaceutical bases are proposed to treat ear diseases in mammals. The silicone base includes silicone, pracaxi oil, and seje oil. Additionally, the NPE composition includes one or more phospholipids, one or more oils rich in essential fatty acids, behenic acid, and oleic acid, one or more skin lipids, and one or more butters rich in linoleic acid and linolenic acid. The synergistic combination of aforementioned natural components exhibit enhanced healing properties, thereby providing organic acids with antioxidant, antibacterial, and antifungal properties. The transdermal pharmaceutical bases are employed to increase the residence time of the medicament in the ear canal, and increase the penetration of the APIs into the affected area, thereby enhancing treatment effectiveness.

18 Claims, 2 Drawing Sheets

TRANSDERMAL PHARMACEUTICAL BASES FOR TREATING EAR DISORDERS

CROSS-REFERENCE TO RELATED APPLICATIONS

This application claims priority to U.S. Provisional Application Ser. No. 62/039,780, filed Aug. 20, 2014, which is hereby incorporated by reference, as well as the benefit of U.S. Provisional Application Ser. No. 62/039,794, filed Aug. 20, 2014, each of which is hereby incorporated by reference herein.

BACKGROUND

Field of the Disclosure

The present disclosure relates generally to pharmaceutical compositions, and more particularly, to transdermal pharmaceutical bases including natural components for treating ear disorders in mammals.

Background Information

Chronic otitis involves inflammation and possibly infection in one or both ears. If left untreated, scar tissue forms and damages the structures of the ear that may result in deafness. Because inflammation often leads to an ear infection, otitis is a painful condition. A variety of ear medications and ear cleaners are available for application into the ears. Sometimes, oral medications (e.g., antibiotics and/or anti-inflammatories) are employed, which may have long term effects. Oral treatments for aforementioned skin conditions have limited clinical use because of the poor solubility and systemic side-effects, therefore, transdermal treatments have received increased attention. However, transdermal treatments possess a limited permeability. This limited permeability reduces the ability to reach the bloodstream and the target area, passing through the stratum corneum.

Chronic otitis in animals is recurrent or persistent inflammation of the ear. One or both ears may be affected. Inflammation of the ear often leads to secondary infection caused by yeast or bacterial overgrowth. This condition is painful and is most often caused by allergies to fleas, certain foods, or substances in the environment. Sometimes medical problems, such as thyroid disease, cause an animal to develop otitis. Certain breeds, such as long ear breeds, are more prone to ear infections.

FIG. 1 is a graphical representation illustrating a canine ear anatomy. In FIG. 1, canine ear anatomy 100 includes vertical canal 102, horizontal canal 104, and tympanic membrane 106. Canines have very unique ear anatomy and ear canals are difficult to treat because of its shape. Vertical canal 102 takes a short turn in order to end up in horizontal canal 104; and horizontal canal 104 ends up in tympanic membrane 106. The average volume of a dog's ear canal is generally filled with about 1.5 mL. Conventional otic preparations generally have a dosage of about 4 to 6 drops, or about 6 to 10 drops once or twice a day; therefore, since about 20 drops are needed to make one mL, dosages of 10 drops or less are not enough to fill the vertical canal 102 or the horizontal canal 104 of a dog. Consequently, there is a need for delivering the right amount of pharmaceutical compositions for treating ear disorders, particularly ear infections.

SUMMARY

The present disclosure refers to transdermal pharmaceutical bases that possess healing properties. Further, these transdermal pharmaceutical bases are proposed for treating ear disorders. In some embodiments, ear disorders include otitis, ear inflammation, and cauliflower ear, among others.

In some embodiments, the transdermal pharmaceutical bases include a silicone base and a natural permeation enhancement (NPE) composition. In these embodiments, the silicone base and the NPE composition include natural components from the Amazon forest, such as, for example pracaxi oil, seje oil, patauá oil, and the like. Further to these embodiments, aforementioned natural components exhibit anti-inflammatory, analgesic, antibacterial, antifungal, and healing properties. In an example, the transdermal pharmaceutical bases include about 50% w/w of the silicone base, and about 50% w/w of the NPE composition.

In another example, the silicone base includes: about 0.5% w/w to 15% w/w of pracaxi oil, preferably from about 1% w/w to 5% w/w; about 0.5% w/w to 15% w/w of seje oil, preferably from about 1% w/w to 5% w/w; about 0.1% w/w to 5% w/w of phosphatidylcholine, preferably from about 0.5% w/w to 2% w/w; and about 10% w/w to 95% w/w of silicone, preferably from about 10% w/w to 50% w/w.

In some embodiments, the NPE composition includes one or more naturally occurring substances, comprising one or more phospholipids, one or more oils rich in essential fatty acids (e.g., behenic and oleic acids), one or more skin lipids, and one or more butters rich in linolenic acid.

In an example, the NPE composition includes a combination of: about 0.05% w/w to 5% w/w of one or more phospholipids, preferably about 2% w/w; about 1% w/w to 20% w/w of one or more oils having essential fatty acids (e.g., behenic and oleic acids), where one of the one or more oils is pracaxi oil, preferably about 3% w/w; about 0.1% w/w to 3% w/w of one or more skin lipids, preferably about 0.5% w/w; and about 1% w/w to 10% w/w of a butter having linoleic and linolenic acids, preferably about 2% w/w.

In another example, the NPE composition includes a combination of: about 10% w/w to 50% w/w of pracaxi oil; about 15% w/w to 40% w/w of patauá oil; about 10% w/w to 30% w/w of inaja oil; and about 10% w/w to 30% w/w of one or more suitable emollients.

In a further example, the NPE composition includes a combination of: about 1% w/w to 20% w/w of pracaxi oil; about 10% w/w to 40% w/w of one or more phospholipids; about 5% w/w to 20% w/w of one or more of patauá oil or inaja oil; and about 5% w/w to 30% w/w of one or more emulsifiers.

In other embodiments, the transdermal pharmaceutical bases include one or more natural components, such as, for example buriti oil, copaiba balsam, bacaba oil, acai oil, ojon oil, andiroba oil, murumuru butter, and/or tucuma oil, among others. In these embodiments, aforementioned natural components improve skin penetration as well as healing properties. In an example, the concentration of each natural component within transdermal pharmaceutical bases is from about 1% w/w to 20% w/w, more preferably about 5% w/w.

In further embodiments, active pharmaceutical ingredients (APIs) are incorporated into the transdermal pharmaceutical bases to formulate transdermal pharmaceutical compositions. In these embodiments, the synergistic effect provided by the combination of aforementioned natural components enables lower dosage requirements of the associated APIs when transdermal pharmaceutical compositions are employed for treating ear disorders. Further to these embodiments, the transdermal pharmaceutical compositions include suitable APIs, such as, for example antibiotic, antifungal, corticosteroids, non-steroidal anti-inflammatories, antibacterials, antivirals, and analgesics, among others.

In some embodiments, the inflammation caused by the disease is reduced by applying a pharmaceutically effective amount of the transdermal pharmaceutical bases. In these embodiments, the transdermal pharmaceutical bases enable an effective administration of specific active pharmaceutical ingredients (APIs), thereby improving treatment outcomes.

In some embodiments, the transdermal pharmaceutical bases are directly administered into the affected area, in a dosage that varies according to the size or weight of the patient (e.g., animals). In these embodiments, a single dose is enough to observe healing within the next 7 days after administration. In an example, small animals need a dose of about 0.5 g of the transdermal pharmaceutical bases. In another example, animals over 100 pounds need a dose of about 2 g to 4 g of the transdermal pharmaceutical base within the infected ear. In this example, the delivery average is of about 1.5 g.

In some embodiments, the transdermal pharmaceutical bases are employed to increase the residence time of the medicament in the ear canal, provide relatively uniform distribution of the base, and can increase the penetration of the APIs in the affected area. In these embodiments, the transdermal pharmaceutical bases enable controlled release of APIs, enhance treatment effectiveness, increase compliance, and are more convenient to use than currently available ear medications.

In some embodiments, transdermal pharmaceutical compositions are manufactured in a range of dosage forms, such as, for example a liquid, solution, cream, gel, lotion, and the like. In other embodiments, transdermal pharmaceutical compositions are manufactured in any form suitable for transdermal application to the internal ear area.

In some embodiments, various additives are included to facilitate the preparation of suitable dosage forms. For example, additives include solvents, penetration enhancers, gelling agents, thickening agents, pH adjusters, preservatives, colors, stabilizing agents, antioxidants, and surfactants, among others.

Numerous other aspects, features, and benefits of the present disclosure may be made apparent from the following detailed description.

BRIEF DESCRIPTION OF THE DRAWINGS

The present disclosure can be better understood by referring to the following figures. The components in the figures are not necessarily to scale, emphasis instead being placed upon illustrating the principles of the disclosure. In the figures, reference numerals designate corresponding parts throughout the different views.

DETAILED DESCRIPTION

Figure 1:
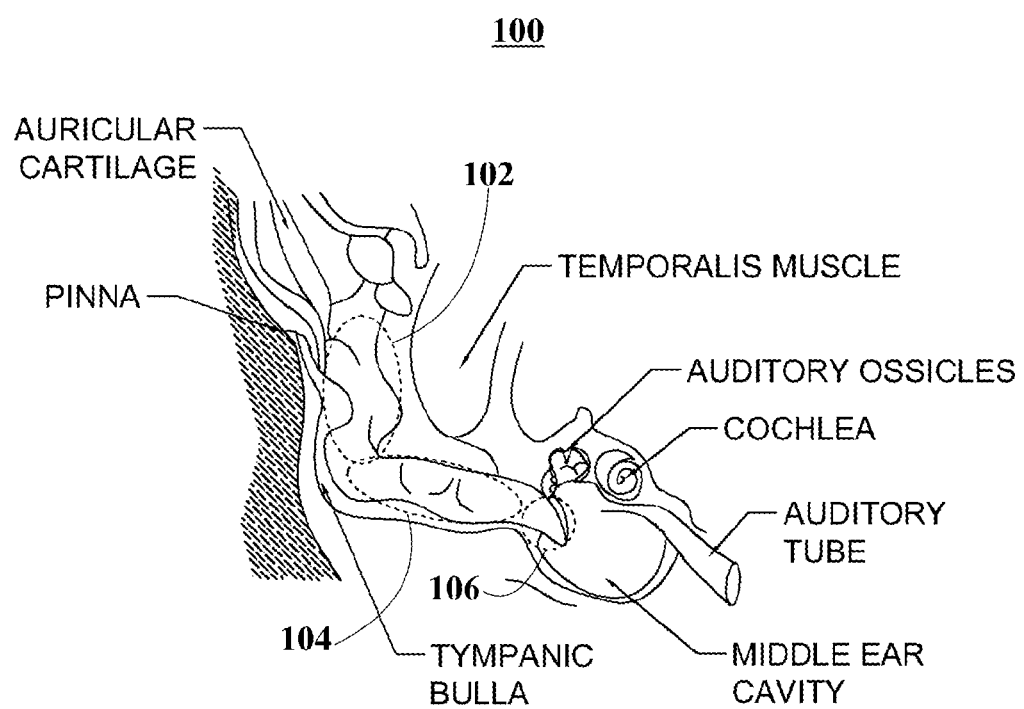
FIG. 1 is a graphical representation illustrating a canine ear anatomy, according to an embodiment.

The present disclosure is here described in detail with reference to embodiments, which form a part here. Other embodiments may be used and/or other changes may be made without departing from the spirit or scope of the present disclosure. The illustrative embodiments described in the detailed description are not meant to be limiting of the subject matter presented here.

Definitions

As used here, the following terms have the following definitions:

"Gel" refers to a colloid in which the solid disperse phase forms a network in combination with that of the fluid continuous phase, thus resulting in a viscous semi-rigid solution.

"Liposomes" refer to spherical, self-enclosed vesicles composed of amphipathic lipids.

"Patient" refers to warm-blooded animals, such as mammals, for example, humans, who are in need of treatment.

"Permeation enhancement" refers to an increase in the permeability of the skin or mucosal tissue to the selected active pharmaceutical ingredient.

"Phospholipids" refer to fat-like organic compounds that resemble triglycerides, but have a fatty acid with a phosphate-containing polar group.

"Scar" refers to a growth of collagen beneath the skin that is formed as the result of wound healing.

"Silicone" refers to polymeric organic silicone compounds obtained as oils.

"Skin lipids" refer to those lipids that are present at the skin's surface.

"Solution" refers to a pharmaceutical preparation consisting of a semisolid emulsion of either the oil-in-water or the water-in-oil type, ordinarily intended for topical or transdermal use.

"Therapeutically effective amount" refers to the amount of subject compound that will elicit the biological or medical response of a tissue, system, animal or human that is being sought.

"Treating" and "Treatment" refers to reduction in severity and/or frequency of symptoms, elimination of symptoms and/or underlying cause, prevention of the occurrence of symptoms and/or their underlying cause, and improvement or remediation of damage.

Description of the Disclosure

The present disclosure refers to transdermal pharmaceutical bases that possess healing properties. Further, these transdermal pharmaceutical bases are proposed for treating ear disorders. In some embodiments, ear disorders include otitis, ear inflammation, and cauliflower ear, among others.

Formulation

In some embodiments, the transdermal pharmaceutical bases include a silicone base and a natural permeation enhancement (NPE) composition. In these embodiments, the silicone base and the NPE composition include natural components from the Amazon forest, such as, for example pracaxi oil, seje oil, patauá oil, and the like. Further to these embodiments, aforementioned natural components exhibit anti-inflammatory, analgesic, antibacterial, antifungal, and healing properties. Still further to these embodiments, aforementioned natural components within transdermal pharmaceutical bases enhance active pharmaceutical ingredients (APIs) penetration to skin or mucosa. In an example, the transdermal pharmaceutical bases include about 50% w/w of the silicone base, and about 50% w/w of the NPE composition.

In another example, the silicone base includes: about 0.5% w/w to 15% w/w of pracaxi oil, preferably from about 1% w/w to 5% w/w; about 0.5% w/w to 15% w/w of seje oil, preferably from about 1% w/w to 5% w/w; about 0.1% w/w to 5% w/w of phosphatidylcholine, preferably from about 0.5% w/w to 2% w/w; and about 10% w/w to 95% w/w of silicone, preferably from about 10% w/w to 50% w/w.

In some embodiments, the NPE composition includes one or more naturally occurring substances, comprising one or more phospholipids, one or more oils rich in essential fatty acids (e.g., behenic and oleic acids), one or more skin lipids, and one or more butters rich in linolenic acid.

In an example, the NPE composition includes a combination of: about 0.05% w/w to 5% w/w of one or more phospholipids, preferably about 2% w/w; about 1% w/w to 20% w/w of one or more oils having essential fatty acids (e.g., behenic and oleic acids), where one of the one or more oils is pracaxi oil, preferably about 3% w/w; about 0.1% w/w to 3% w/w of one or more skin lipids, preferably about 0.5% w/w; and about 1% w/w to 10% w/w of a butter having linoleic and linolenic acids, preferably about 2% w/w.

In another example, the NPE composition includes a combination of: about 10% w/w to 50% w/w of pracaxi oil; about 15% w/w to 40% w/w of patauá oil; about 10% w/w to 30% w/w of inaja oil; and about 10% w/w to 30% w/w of one or more suitable emollients.

In a further example, the NPE composition includes a combination of: about 1% w/w to 20% w/w of pracaxi oil; about 10% w/w to 40% w/w of one or more phospholipids; about 5% w/w to 20% w/w of one or more of patauá oil or inaja oil; and about 5% w/w to 30% w/w of one or more emulsifiers.

Silicone Base

In some embodiments, the silicone base includes silicone, pracaxi oil, and seje oil. In these embodiments, the silicone base possesses unique ingredients that give, to the treatment, potential healing and soothing power, emolliency, and mild penetration. Further to these embodiments, the silicone base enables the penetration of APIs through the skin. In these embodiments, the aforementioned components within the silicone base are oils that are rich sources of essential fatty acids, such as, for example behenic acid, oleic acid, and in some instances, lauric acid.

Pracaxi Oil

Pracaxi oil is obtained from the seed oil of the Pentaclethara macroloba tree, or pracaxi tree. The pracaxi tree is a deciduous tree from the legumes family, growing in altitudes below 600 meters in many parts of northern Brazil, Guyana, Trinidad, and parts of Central America, and may reach between about 8 and about 35 meters in height. Pracaxi trees may sometimes be found in wetlands, and are resistant to water logging.

Pracaxi seeds include from about 45% to 48% fat, about 27% to 28% protein, and about 12% to 14% carbohydrates (see Table 1). Pracaxi seed oil includes the highest known natural concentration of behenic acid (about 20%) in a vegetable fat, more than six times higher than in peanut oil, and also includes about 35% of oleic acid. In some cases, pracaxi seed oil may include greater percentages of the aforementioned behenic acid and oleic acid. The oleic acid and lauric acid, contained within pracaxi oil are effective vehicles for delivering drugs through the skin.

TABLE 1

General composition of pracaxi oil.

| Components | Composition % |
| --- | --- |
| Fat | 45-48 |
| Protein | 27-28 |
| Carbohydrates | 12-14 |

In an example, the fatty acid composition of the pracaxi oil is illustrated below in Table 2. Compositions vary depending on the region and conditions in which the pracaxi tree grows.

TABLE 2

Fatty acid composition of the pracaxi oil.

| Fatty Acids | Carbon Atoms | Compositions % |
| --- | --- | --- |
| Lauric | 12:00 | 1.30 |
| Myristic | 14:00 | 1.21 |
| Palmitic | 16:00 | 2.04 |
| Stearic | 18:00 | 2.14 |
| Oleic | 18:10 | 44.32 |
| Linoleic | 18:20 | 1.96 |
| Linolenic | 18:30 | 2.31 |
| Behenic | 22:00 | 9.67 |
| Lignoceric | 24:00 | 14.81 |

TABLE 3

Specifications of the pracaxi oil.

| Indicators | Reference Value |
| --- | --- |
| Texture | Solid below 18.5° C., liquid viscous texture above this temperatures |
| Color | Translucent yellow, yellowish-white when solid |
| Odor | Almost odorless |
| Melting point | 18.5° C. |
| Refractive index (40° C.) | 1.4690 |
| Iodine value | 65-70 g 12/100 g |
| Saponification value | 170-180 mg KOH/g |
| Acid value | 3-5 mg KOH/g |
| Peroxide value | 5-10 mEQ/kg |
| Density (25°) | 0.917 g/cm$^3$ |

Pracaxi oil has been widely employed within pharmaceutical compositions because of its cosmetic, therapeutic, and medicinal properties. Pracaxi oil is rich in organic acids with antioxidant, antibacterial, antiviral, antiseptic, antifungal, anti-parasitic, and anti-hemorrhagic properties. Because pracaxi oil possesses many of the aforementioned properties, pracaxi oil can be suitable for treating ear disorders.

Pataua Oil

Pataua oil, also called seje oil, is extracted from the mesocarp of the patauá palm and generally appears as a greenish-yellow and transparent liquid, with little odor and taste, possessing the physical appearance and composition of fatty acids that are similar to olive oil (*Oleg europaea*). Pataua oil has a high content of unsaturated fatty acids (see Table 4). Pataua oil also has a high content of oleic acid, which enables patauá oil to be used as skin moisturizer. The dry mesocarp of patauá palm includes about 7.4% protein and possesses an excellent amino acid composition. Because of this, the protein of patauá is one of the most valuable found among plants and may be compared with the meat or milk from cattle. The most abundant sterols found within pataua oil are $\Delta^5$avenosterol and β-sitosterol, with relative contents of about 35% and about 38%, respectively. The most abundant aliphatic alcohols found within pataua oil are those with 7, 8, and 10 carbon atoms. Among tocopherols found within pataua oil, α-tocopherol was predominant Aldehydes, such as heptanal, octanal and decanal, were present in the volatile fraction of pataua oil along with terpenoid compounds.

TABLE 4

Fatty acid composition of pataua oil.

| Fatty Acids | Carbon Atoms | Composition % |
|---|---|---|
| Palmitic | 16:00 | 13.2 |
| Palmitoleic | 16:10 | — |
| Stearic | 18:00 | 3.6 |
| Oleic | 18:10 | 77.7 |
| Linoleic | 18:20 | 2.7 |
| Linolenic | 18:30 | 0.6 |
| Arachidic | 20:00 | 2 |
| Unsaturated | | 81.6 |

Natural Permeation Enhancement (NPE) Composition

In some embodiments, the NPE composition includes one or more naturally occurring substances, comprising one or more phospholipids, one or more oils rich in essential fatty acids (e.g., behenic and oleic acids), one or more skin lipids, and one or more butters rich in linolenic acid.

In some embodiments, the NPE composition is employed as a penetration enhancer for a number of different compositions, including topical cosmetics and pharmaceutical formulations. In these embodiments, the NPE composition includes natural ingredients that assist with penetration of APIs through the skin. Further to these embodiments, the NPE composition having fatty acid micro-particles include behenic acid, oleic acid, omega-3 fatty acids, and phospholipids, among others. Still further to these embodiments, the use of the NPE composition may eliminate the need for pre-encapsulation of the APIs.

In some embodiments, the aforementioned components within NPE composition act synergistically to increase the skin permeation of water and oil soluble products. In these embodiments, the NPE composition, which is a solution, is added to a gel or emulsion at a given percent to give permeation power to the otherwise transdermal formulation. Further to these embodiments, when the NPE composition is formulated, liposomes are formed from the fatty acids, including behenic and oleic acids that are present in the one or more oils, and are stabilized by the phospholipids within the composition. Still further to these embodiments, when the NPE composition is added to water or a water-incorporating composition, liposomes are formed.

In some embodiments, the liposomes are filled with drugs or other APIs. In these embodiments, the liposomes include naturally-derived phospholipids with mixed lipid chains or other surfactants. Further to these embodiments, the liposomes that are formed are used to deliver drugs or other APIs transdermally to the skin's surface. In these embodiments, some molecules having a low molecular weight, such as glucose, to those having a high molecular weight, such as peptides and proteins, are incorporated within liposomes. Further to these embodiments, water soluble compounds/drugs are present in aqueous compartments while lipid soluble compounds/drugs and amphiphilic compounds/drugs insert themselves within phospholipid bilayers.

In some embodiments, the oils within the NPE composition are rich sources of essential fatty acids, such as behenic and oleic acids. In these embodiments, the supply of essential fatty acids and antioxidant molecules restore the cutaneous permeability and the function of the skin barrier. Further to these embodiments, the supply of essential fatty acids and antioxidant molecules contribute to the control of the imperceptible water loss and maintain moisture of the skin. In an example, the NPE composition includes pracaxi oil, which fatty acid composition is illustrated in Table 2.

Inaja Oil

Inaja oil is extracted from a tree called *Maximiliana maripapalm*, or Inaja. Inaja has one of the highest sources of lauric acid (greater than about 40% w/w) and oleic acid (greater than about 15% w/w). Further, the highest concentration of fatty acids found within the Inaja is found in the kernal oil, as opposed to the pulp oil. Inaja is an indigenous Amazonian palm widespread in the state of Pará, growing around the Amazon River estuary. Oil from Inaja is extracted from the fruits of the Inaja palm, which includes about 70% w/w short-chain fatty acids, including lauric acid and myristic acid. This palm has been used in the production of bar soap because of its high concentration of lauric acid. The fatty acid composition of inaja kernel oil is illustrated below in Table 5.

TABLE 5

Fatty acid composition of Inaja kernel oil.

| Fatty Acids | Carbon Atoms | Composition % |
|---|---|---|
| Lauric | 12:00 | 40.5000 |
| Myristic | 14:00 | 25.0000 |
| Palmitic | 16:00 | 9.0000 |
| Stearic | 18:00 | 2.4000 |
| Oleic | 18:10 | 10.8000 |
| Linoleic | 18:20 | 1.9600 |
| Linolenic | 18:30 | 2.4000 |
| Behenic | 22:00 | trace |
| Lignoceric | 24:00 | trace |

Additionally, behenic acid, lauric acid, oleic acid, and other fatty acids produces irritation when directly applied onto the skin, thereby producing skin irritation. But, when aforementioned acids are present within oils (e.g., pracaxi oil and/or inaja oil), the acids work to enhance the restoration of cutaneous barrier organization and epidermal elasticity, in addition to contributing to the control of imperceptible water loss, thereby maintaining skin hydration. This is, at least in part, due to the high amounts of essential fatty acids within aforementioned oils. The link between skin permeation and hydration is improved. Increasing the permeability of the stratum corneum is achieved by the increase of water content within this tissue. Hydration by occlusion causes a swelling of the corneocytes and, subsequently, increases the skin permeation of actives. Here, the utilization of physiological lipids, essential fatty acids, and phospholipids, provide penetration power with restorative benefits to the skin. In some embodiments, other oils are used in alternative compositions, including pataua oil, which fatty acid composition is illustrated in Table 4.

Skin Lipids

In some embodiments, the NPE composition includes skin lipids. Examples of skin lipids within NPE composition include ceramides and/or squalene. Ceramides are the major lipid constituents of lamellar sheets. Ceramides are a structurally heterogeneous and complex group of sphingolipids including derivatives of sphingosine bases in amide linkage with a variety of fatty acids. Differences in chain length, type, and extent of hydroxylation and saturation are responsible for the heterogeneity of the epidermal sphingolipids. Ceramides play an important role in structuring and maintaining the water permeability barrier function of the skin. In conjunction with the other stratum corneum lipids, they form ordered structures. A structured semi-occlusive barrier that increases skin hydration is a positive influence on the penetration of APIs. In these embodiments, another skin lipid that is used is squalene, which is a lipid fat in the skin.

Further to these embodiments, when squalene is used together with a ceramide and a phospholipid, such as phosphatidylcholine, the formulation is mild and is used on even sensitive skin. In these embodiments, squalene helps to decrease water evaporation, thereby speeding up skin permeation of actives and decreasing irritation made by surfactants found in emulsions. Further to these embodiments, squalene, being a natural emollient, imparts an elegant feel to formulations in which it is used. Still further to these embodiments, squalene helps skin to retain moisture and feel soft and conditioned without feeling greasy.

Butters

In some embodiments, the NPE composition includes butters rich in linoleic acid and linolenic acid. In an example, the butter employed within NPE composition is Butyrospermum parkii butter, also known as shea butter. In other embodiments, butters include cupuacu butter, buriti butter, passionfruit butter, mango butter, tucuma butter, palm butter, murumu butter, chamomile butter, cocoa butter, orange butter, lemon grass butter, avocado butter, tamanu butter, aloe butter, shea butter, monoi butter, pomegranate butter, almond butter, jojoba butter, red palm butter, acai butter, olive butter, matcha green tea butter, brazil nut butter, macadamia butter, kokum butter, mafura butter, coffee butter, tucuma butter, ucuuba butter, bacuri butter, chamomile butter, and the like.

In other embodiments, the transdermal pharmaceutical bases include one or more natural components, such as, for example buriti oil, copaiba balsam, bacaba oil, acai oil, ojon oil, andiroba oil, murumuru butter, and/or tucuma oil, among others. In these embodiments, aforementioned natural components improve skin penetration as well as healing properties. In an example, the concentration of each natural component within transdermal pharmaceutical bases is from about 1% w/w to 20% w/w, more preferably about 5% w/w.

In further embodiments, active pharmaceutical ingredients (APIs) are incorporated into the transdermal pharmaceutical bases to formulate transdermal pharmaceutical compositions. In these embodiments, the synergistic effect provided by the combination of aforementioned natural components enables lower dosage requirements of the associated APIs when transdermal pharmaceutical compositions are employed for treating ear disorders. Further to these embodiments, the transdermal pharmaceutical compositions include suitable APIs, such as, for example antibiotic, antifungal, corticosteroids, non-steroidal anti-inflammatories, antibacterials, antivirals, and analgesics, among others.

Administration

In some embodiments, the transdermal pharmaceutical bases are employed as inflammation reduction formulations. In these embodiments, the transdermal pharmaceutical bases are employed for treating inflammations caused by ear diseases, such as chronic otitis, and the like. Further to these embodiments, the transdermal pharmaceutical bases exhibit healing and soothing power, emolliency, and mild penetration. In other embodiments, the transdermal pharmaceutical bases are employed for treating ear infections.

In some embodiments, the transdermal pharmaceutical bases are directly administered into the affected area. In these embodiments, the transdermal pharmaceutical bases are applied into the affected area in order to access to the internal ear infection area.

In some embodiments, the transdermal pharmaceutical base dosages vary according to the animal size or weight. In an example, small animals need a dose of about 0.5 g of the transdermal pharmaceutical bases, which is applied using suitable methods (e.g., hand application, calibrated devices, and the like). In another example, animals over 100 pounds need a dose of about 2 g to 4 g of the transdermal pharmaceutical base within the infected ear. In this example, the delivery average is of about 1.5 g.

In some embodiments, transdermal pharmaceutical compositions are manufactured in a range of dosage forms, such as, for example a liquid, solution, cream, gel, lotion, and the like. In other embodiments, transdermal pharmaceutical compositions are manufactured in any form suitable for transdermal application to the internal ear area.

In some embodiments, transdermal pharmaceutical bases are applied manually with or without an applicator, such as, for example a dropper or pipette; an applicator, such as, for example a swab, brush, cloth, pad, and sponge, among others; or with any other applicator, such as, for example a solid support including paper, cardboard or a laminate material, including material with flocked, glued or otherwise fixed fibers, among others.

In other embodiments, transdermal pharmaceutical bases are applied as an aerosol or non-aerosol spray from a pressurized or non-pressurized container. In further embodiments, transdermal pharmaceutical bases are administered in metered doses, such as, for example from a metered dose applicator or from an applicator including a single dose of disclosed transdermal pharmaceutical bases.

In some embodiments, the aforementioned natural components within transdermal pharmaceutical bases act synergistically to increase the skin permeation of water and oil soluble products. In these embodiments, when the NPE composition is prepared, liposomes are formed from the fatty acids, including behenic acid and oleic acid that are present on one or more oils, and are stabilized by the phospholipids within the silicone base. Further to these embodiments, by increasing the permeability of the transdermal pharmaceutical bases the time of treatment is significantly reduced, thereby reducing the time to obtain therapeutic results to a period of about 7 days.

In some embodiments, the transdermal pharmaceutical bases are employed to increase the residence time of the medicament in the ear canal, provide relatively uniform distribution of the base, and can increase the penetration of the APIs in the affected area. In these embodiments, the transdermal pharmaceutical bases enable controlled release of APIs, enhance treatment effectiveness, increase compliance, and are more convenient to use than currently available ear medications.

In an example, the transdermal pharmaceutical composition is an otic pharmaceutical formulation. In this example, the otic pharmaceutical formulation is employed for treating an infection within a canine's internal ear.

Figure 2:
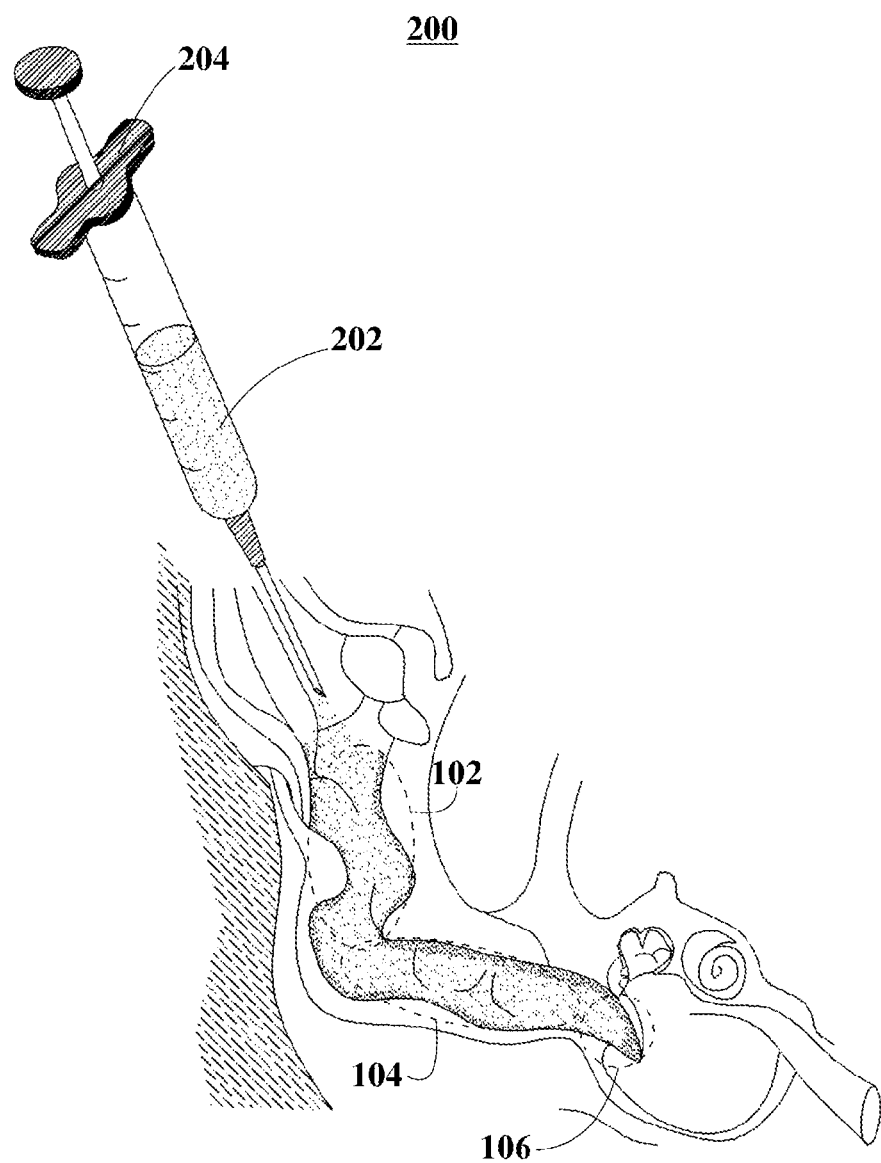
FIG. 2 is a graphical representation illustrating the application of an otic pharmaceutical formulation into an infected area of a canine's internal ear, according to an embodiment.

FIG. 2 is a graphical representation illustrating the application of an otic pharmaceutical formulation into an infected area of a canine's internal ear. In FIG. 2, administration technique 200 illustrates otic pharmaceutical formulation 202, delivery device 204, vertical canal 102, horizontal canal 104, and tympanic membrane 106. In FIG. 2, elements having identical element numbers from previous figures perform in a substantially similar manner.

In some embodiments, otic pharmaceutical formulation 202 is applied into the affected area. In these embodiments, the dosage of otic pharmaceutical formulation 202 varies according to the animal size or weight. In an example, small animals need a dose of about 0.5 g of otic pharmaceutical formulation 202. In another example, animals over 100 pounds need a dose of about 2 g to 4 g of otic pharmaceutical gel 202 in the infected ear. In this example, the delivery average is of about 1.5 g. Further to these embodiments, otic pharmaceutical formulation 202 is applied by employing calibrated delivery device 204.

In some embodiments, various additives are included to facilitate the preparation of suitable dosage forms. For example, additives include solvents, penetration enhancers, gelling agents, thickening agents, pH adjusters, preservatives, colors, stabilizing agents, antioxidants, and surfactants, among others.

While various aspects and embodiments have been disclosed, other aspects and embodiments are contemplated. The various aspects and embodiments disclosed are for purposes of illustration and are not intended to be limiting, with the true scope and spirit being indicated by the following claims.

What is claimed is:

1. A transdermal pharmaceutical composition comprising:
    a silicone base including about 0.5% w/w to about 15% w/w pracaxi oil, about 0.5% w/w to about 15% w/w seje oil, and about 10% w/w to about 95% w/w silicone together in a synergistically effective total amount; and
    a pharmaceutically effective amount of at least one active pharmaceutical ingredient.

2. The transdermal pharmaceutical composition of claim 1, wherein the silicone base further includes about 0.1% w/w to about 5% w/w phosphatidylcholine.

3. The transdermal pharmaceutical composition of claim 1, wherein the silicone base includes about 1% w/w to about 5% w/w pracaxi oil, about 1% w/w to about 5% w/w of seje oil, about 10% w/w to about 50% w/w silicone, and about 0.1% w/w to about 5% w/w of phosphatidylcholine.

4. The transdermal pharmaceutical composition of claim 2, wherein the silicone base includes about 0.5% w/w to about 2% w/w phosphatidylcholine.

5. The transdermal pharmaceutical composition of claim 1, wherein the transdermal pharmaceutical composition comprises at least one substance selected from the group consisting of: at least one phospholipid, at least one oil including behenic acid and oleic acid, at least one skin lipid, and at least one butter including linolenic acid.

6. The transdermal pharmaceutical composition of claim 1, wherein the transdermal pharmaceutical composition comprises about 0.05% w/w to about 5% w/w of at least one phospholipid, about 1% w/w to about 20% w/w of at least one oil including behenic acid and oleic acid, about 0.1% w/w to about 3% w/w of at least one skin lipid, and about 1% w/w to about 10% w/w of at least one butter including linolenic acid.

7. The transdermal pharmaceutical composition of claim 6, wherein the transdermal pharmaceutical composition comprises about 2% w/w to about 5% w/w of the at least one phospholipid.

8. The transdermal pharmaceutical composition of claim 6, wherein the transdermal pharmaceutical composition comprises about 3% w/w of the at least one oil including behenic acid and oleic acid.

9. The transdermal pharmaceutical composition of claim 6, wherein the transdermal pharmaceutical composition comprises about 0.5% of the at least one skin lipid.

10. The transdermal pharmaceutical composition of claim 6, wherein the transdermal pharmaceutical composition comprises about 2% w/w of the at least one butter including linolenic acid.

11. The transdermal pharmaceutical composition of claim 6, wherein the transdermal pharmaceutical composition comprises about 2% w/w to about 5% w/w of the at least one phospholipid, about 3% w/w of the at least one oil including behenic acid and oleic acid, about 0.5% of the at least one skin lipid, and about 2% w/w of the at least one butter including linolenic acid.

12. The transdermal pharmaceutical composition of claim 1, wherein the transdermal pharmaceutical composition comprises about 10% w/w to about 50% w/w of pracaxi oil, patauá oil, and inaja oil.

13. The transdermal pharmaceutical composition of claim 12, wherein the transdermal pharmaceutical comprises about 15% w/w to about 40% w/w of the patauá oil, and about 10% w/w to about 30% w/w of the inaja oil.

14. The transdermal pharmaceutical composition of claim 12, wherein the transdermal pharmaceutical composition comprises about 1% w/w to about 15% w/w of pracaxi oil, about 10% w/w to about 40% w/w of at least one phospholipid, about 5% w/w to about 20% w/w of the patauá oil, about 5% w/w to about 20% w/w of the inaja oil, and about 5% w/w to about 30% w/w of at least one emulsifier.

15. The transdermal pharmaceutical composition of claim 1, wherein the silicone base further comprises at least one natural component selected from the group consisting of buriti oil, copaiba balsam, bacaba oil, acai oil, ojon oil, andiroba oil, murumuru butter, and tucuma oil.

16. The transdermal pharmaceutical composition of claim 1, wherein the silicone base further comprises at least one natural component selected from the group consisting of about 1% w/w to about 20% w/w buriti oil, about 1% w/w to about 20% w/w copaiba balsam, about 1% w/w to about 20% w/w bacaba oil, about 1% w/w to about 20% w/w acai oil, about 1% w/w to about 20% w/w ojon oil, about 1% w/w to about 20% w/w andiroba oil, about 1% w/w to about 20% w/w murumuru butter, and about 1% w/w to about 20% w/w tucuma oil.

17. The transdermal pharmaceutical composition of claim 1, wherein the silicone base further comprises at least one natural component selected from the group consisting of about 5% w/w buriti oil, about 5% w/w copaiba balsam, about 5% w/w bacaba oil, about 5% w/w acai oil, about 5% w/w ojon oil, about 5% w/w andiroba oil, about 5% w/w murumuru butter, and about 5% w/w tucuma oil.

18. The transdermal pharmaceutical composition of claim 1, wherein the transdermal pharmaceutical composition is selected from the group consisting of a liquid, a solution, a cream, a gel, and a lotion.

* * * * *